United States Patent [19]
Javidi

[11] Patent Number: 4,832,447
[45] Date of Patent: May 23, 1989

[54] JOINT TRANSFORM IMAGE CORRELATION USING A NONLINEAR SPATIAL LIGHT MODULATOR AT THE FOURIER PLANE

[75] Inventor: Bahram Javidi, East Lansing, Mich.

[73] Assignee: Board of Trustees operating Michigan State University, East Lansing, Mich.

[21] Appl. No.: 128,803

[22] Filed: Dec. 4, 1987

[51] Int. Cl.$^4$ .................. G02B 27/46; G06G 9/00
[52] U.S. Cl. .................. 350/162.13; 364/822
[58] Field of Search .................. 350/162.13, 162.14; 364/822

[56] References Cited

U.S. PATENT DOCUMENTS

| | | | |
|---|---|---|---|
| 4,695,973 | 9/1987 | Yu | 350/162.13 |
| 4,765,714 | 8/1988 | Horner et al. | 350/162.13 |

Primary Examiner—Bruce Y. Arnold
Attorney, Agent, or Firm—Ian C. McLeod

[57] ABSTRACT

The present invention is a nonlinear joint transform image correlator which employs a spatial modulator operating in a binary mode at the Fourier plane. The reference and input images are illuminated by a coherent light at the object plane of a Fourier transform lens system. A image detection device, such as a charge coupled device, is disposed at the Fourier plane of this Fourier transform lens system. A thresholding network detects the median intensity level of the imaging cells of the charge coupled device at the Fourier plane and binarizes the Fourier transform interference intensity. The correlation output is formed by an inverse Fourier transform of this binarized Fourier transform interference intensity. In the preferred embodiment this is achieved via a second Fourier transform lens system. This binary data is then applied to spatial light modulator device operating in a binary mode located at the object plane of a second Fourier transform lens system. This binary mode spatial light modulator device is illuminated by coherent light producing the correlation output at the Fourier plane of the second Fourier transform lens system. The inverse Fourier transform may also be formed via a computer. In an alternative embodiment, the Fourier transform interference intensity is thresholded into one of three ranges. An inverse Fourier transform of this trinary Fourier transform interference intensity produces the correlation output.

17 Claims, 5 Drawing Sheets

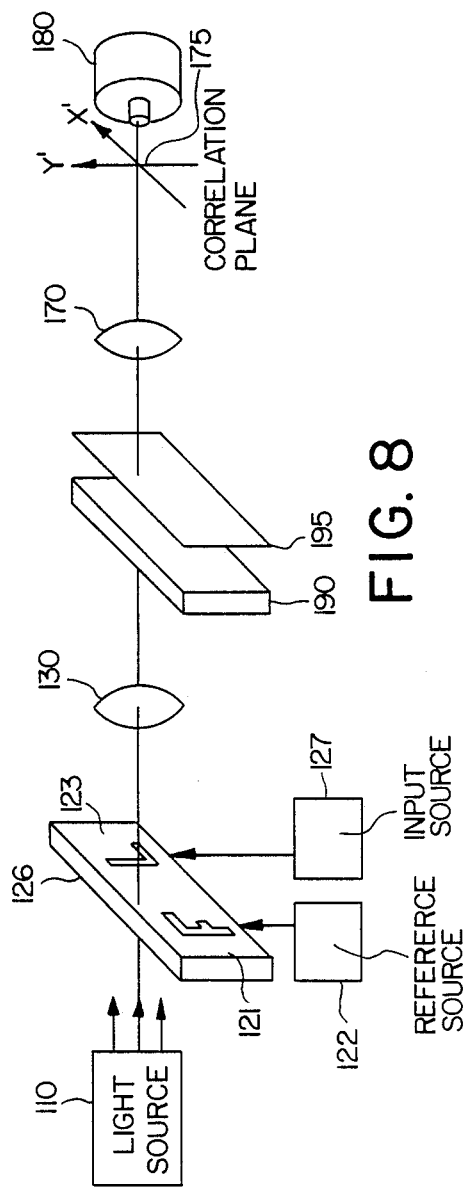
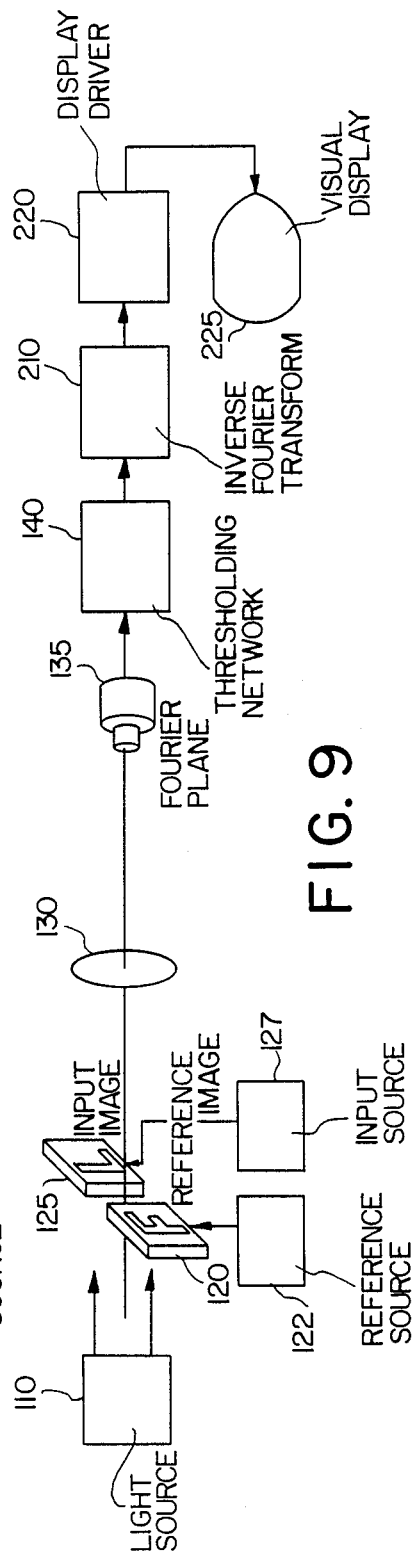

JOINT TRANSFORM IMAGE CORRELATION USING A NONLINEAR SPATIAL LIGHT MODULATOR AT THE FOURIER PLANE

TECHNICAL FIELD OF THE INVENTION

The technical field of the present invention is that of optical pattern recognition systems using joint transform image correlation, and in particular joint transform image correlation systems which employ nonlinear optics at the Fourier plane to quantize the Fourier transform interference intensity.

BACKGROUND OF THE INVENTION

Optical pattern recognition based on image correlation is highly useful in automatic inspection, testing, surveillance and robotic vision. Image correlation involves the detailed comparison of an input image with a reference image. This detailed comparison can yield information regarding the similarity of the input image and the reference image. This technique may be useful for identification of radar or sonar images or for identification of parts via a machine vision system.

Coherent optical systems can provide high speed processing of images with large space-bandwidth products. It would be highly useful to develop optical correlator systems that produce correlation signals with large peak intensity, narrow correlation bandwidth, small auto-correlation sidelobes and good discrimination sensitivity.

SUMMARY OF THE INVENTION

The present invention is a nonlinear joint transform image correlator which employs a spatial modulator operating in a binary mode in the Fourier plane. The reference and input images are illuminated by a coherent light at the object plane of a Fourier transform lens system. A image detection device, such as a charge coupled device, is disposed at the Fourier plane of this Fourier transform lens system to detect the intensity of the Fourier transform interference between the input images. A thresholding network detects the median intensity level of the imaging cells of the charge coupled device at the Fourier plane. The thresholding network then generates a binary output for each pixel of the Fourier transform interference intensity indicating whether the image intensity of that pixel is greater than the median intensity.

The correlation output of the device is provided by an inverse Fourier transform of the binarized Fourier transform interference intensity. In the preferred embodiment of the present invention this binary data corresponding to the image on the Fourier plane is then applied to a spatial light modulator device operating in a binary mode having an array of pixels similar to the imaging device. This spatial light modulator device operating in a binary mode is located at the object plane of a second Fourier transform lens system. This spatial light modulator device operating in a binary mode is illuminated by coherent light which causes an image to form at the Fourier plane of the second Fourier transform lens system. The output of the joint transform image correlator is read at this Fourier plane. In an alternative embodiment, the inverse Fourier transform is performed electrically via a computer.

This technique results in the quantization and binarization of the interference intensity at the Fourier plane of the first Fourier transform lens system. It has been found that, far from causing deterioration of the quality of the correlation signals at the output plane, the performance of the binary mode joint transform correlation is greatly enhanced and the correlation peak value is significantly increased. Compared to conventional optical correlator systems, the nonlinear optical correlator of this invention provides substantially better performance in terms of the auto-correlation peak intensity, bandwidth and sidelobe intensity. Furthermore, the system of this invention out performs conventional optical correlators in terms of discrimination sensitivity.

BRIEF DESCRIPTION OF THE DRAWINGS

These and other objects and aspects of the present invention will become clear from the following description of the invention take in conjunction with the drawings, in which:

FIG. 8 illustrates schematically the structure of the nonlinear joint transform image correlator in accordance with an alternative embodiment of the present invention; and FIG. 9 illustrates schematically the structure of the nonlinear joint transform image correlator in accordance with a still further embodiment of the present invention;

DETAILED DESCRIPTION OF THE PREFERRED EMBODIMENT

Figure 1:
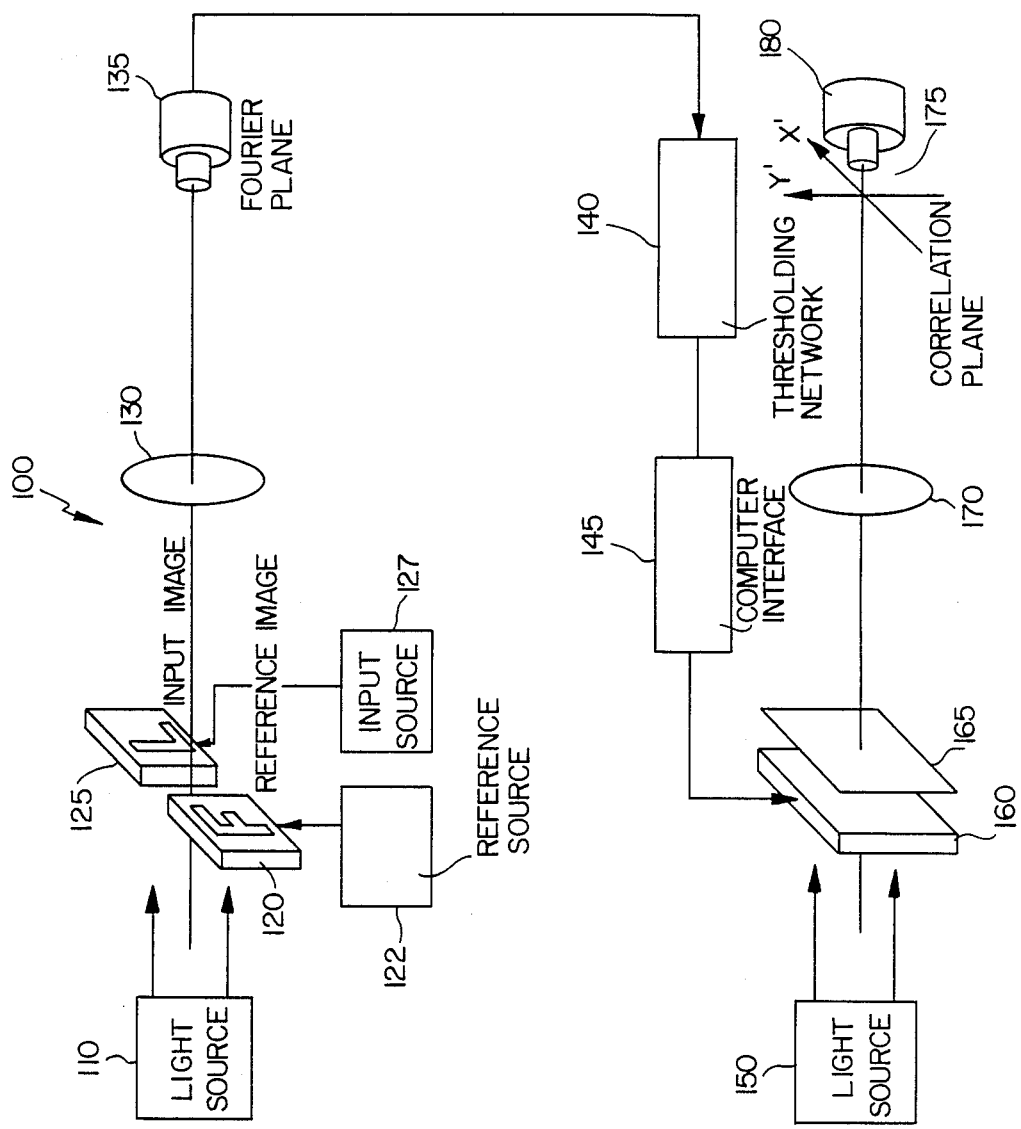
FIG. 1 illustrates schematically the structure of the nonlinear joint transform image correlator of the present invention.

FIG. 1 illustrates the nonlinear joint transform image correlator of the present invention in schematic form. A light source 110 generates coherent light for illumination of a pair of spatial light modulators 120 and 125. Spatial light modulators 120 and 125 provide the reference and input images, respectively, to the correlation system. Light source 110 would typically include a laser light source and suitable optical elements to produce a collimated beam of the size necessary to illuminate both spatial light modulators 120 and 125. Although two spatial light modulators are illustrated in FIG. 1, those skilled in the art would realize it is equally feasible to employ suitably controlled separate sections of a single spatial light modulator to provide the necessary images.

The image inputs to the apparatus are provided by spatial light modulators 120 and 125 located at an input plane. Spatial light modulator 120 provides the reference image. In the example illustrated in FIG. 1 this reference image corresponds to the character "F". Spatial light modulator 125 provides the input image. In the example illustrated in FIG. 1 this input image corresponds to the character "L". These images are controlled by reference image source 122 and input image source 127, respectively. The specification of the reference and input images is in accordance with the prior art and is beyond the scope of this invention. It is expected that either optically addressed or electrically addressed spatial light modulators can be employed at the input plane as spatial light modulators 120 and 125. The essential feature is that spatial light modulators 120 and 125 provide coherent images displayed at the same plane. As noted above it is equally feasible to provide a single spatial light modulator having separately controlled sections for the reference and input images.

The plane of spatial light modulators 120 and 125 is the object plane of Fourier transform lens system 130. Fourier transform lens system receives the coherent light from the spatial light modulators 120 and 125 and produces an interference of these two images at its Fourier plane.

An imaging device 135 is located at this Fourier plane to convert the interference intensity into an electrical signal. In accordance with the preferred embodiment imaging device 135 is a charge coupled device. A charge coupled device generates a charge on each cell of a plurality of imaging cells which is proportional to light intensity. After a timed exposure the charge coupled device can be read by transferring the accumulated charge by rows to an output. This produces an analog electrical signal proportional to the light intensity during the exposure. In the preferred embodiment, this analog electrical signal is read out in a raster scan fashion to produce an indication of the interference intensity at each imaging cell of the charge coupled device.

Figure 2:
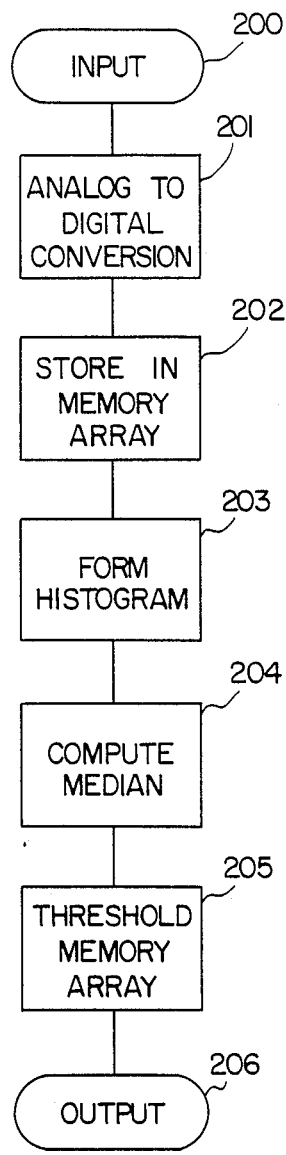
FIG. 2 illustrates in flow chart form the process of the thresholding network illustrated in FIG. 1.

The output of the imaging device 135 is applied to a thresholding network 140. Thresholding network 140 is preferably a computer circuit which quantizes and binarizes the output of the imaging device. This process occurs in accordance with the flow chart illustrated in FIG. 2. Firstly, the analog output from the imaging device 135 is input into the thresholding network (block 200) and digitized via an analog-to-digital converter (block 201). This provides a digital signals for each imaging cell which can be manipulated via computer circuits. The set of digital signals is stored in a memory array, with one location of the memory array provided to store the digital signal of a corresponding one of the imaging cells (block 202).

The thresholding network then forms a histogram of the intensity values on the imaging cells represented by the digital signals stored in the memory array (block 203). This histogram is formed by counting the number of digital signals within the memory array of each permissible digital value. Next the median of these digital signals is computed (block 204). The median is the digital value which is above the value of half the digital signals and below the value of half the digital signals.

A new memory array is formed from the original memory array by binarizing the original digital signals (block 205). If the value of the digital signal of a particular memory location of the memory array is above the computed median value, then the corresponding memory location of the new memory array is given a first binary value. Otherwise that memory location of the new array is give the opposite binary value. This process could occur by the formation of a second, similar sized memory array or by replacement of the digital values in the original memory array. Lastly, data in the new memory array is output (block 206).

The process described above could be performed in a number of ways. It is feasible to construct special purpose computer circuits to perform these tasks. Alternatively, a general purpose computer could be programmed to perform these functions as a subset of other tasks. In any event, thresholding network 140 produces a set of binary values corresponding to the thresholded interference intensity measured by imaging device 130.

The correlation output of the nonlinear joint transform image correlator of the present invention is formed by an inverse Fourier transform of the thresholded interference intensity. This inverse Fourier transform may be achieved in a number of ways. Below is described an optical system for achieving this inverse Fourier transform. Such an optic system has the advantage of providing high speed processing of images of large space-bandwidth products.

Computer interface 145 serves to connect thresholding network 140 and spatial light modulator device in the binary mode 160. Spatial light modulator device in the binary mode 160 is a spatial light modulator operating in a binary mode which has an array of spatial light modulation cells corresponding to the array of imaging cells of the imaging device 135. Computer interface 145 couples the binary values of the new memory array to the corresponding spatial light modulation cells of spatial light modulator device in the binary mode 160.

There are several alternatives to embody spatial light modulator in the binary mode 160. Spatial light modulator in the binary mode 160 can be embodied by a magneto-optic device, a deformable mirror device or a liquid crystal device.

In accordance with one embodiment of the present invention spatial light modulator device in the binary mode 160 is a magneto-optic device. A magneto-optic device provides controlled rotation of the polarization of light transmitted through individual spatial light modulation cells dependent upon the electrical signal applied to the that cell. Provided that the light from second light source 150 is linearly polarized, and linear polarizer 165 is provided, a binary drive to the cells of a magneto-optic device can provide binary spatial light modulation. Light transmitted through the magneto-optic device will have a polarization parallel to or perpendicular to the direction of polarization of polarizer 165 dependent upon the electrical signal applied to that cell. The light from light source 150 is thereby either transmitted or blocked, respectively. Thus each cell is substantially transparent or substantially opaque in accordance with the binary value of the corresponding memory location of the new memory array.

In accordance with another embodiment of the present invention spatial light modulator device in the binary mode 160 is a deformable mirror device. Such deformable mirror devices have a an array of cells including thin reflective membranes which are deformed in proportion to the charge on that particular cell. Light reflected from such cells undergoes a phase shift which is proportional to the deformation controlled light path length and hence to the electrical drive signal applied to that cell. These deformable mirror devices can be employed using linearly polarized light and a linear polarizer in the manner discussed above with regard to magneto-optic devices to provide spatial light modulation in a binary mode. Such deformable mirror devices operate in reflection rather than transmission as in the case of magneto-optic devices, and as illustrated in FIG. 1. However, the change from operating in transmission to operating in reflection is well known in the optical art.

In accordance with a further embodiment of the present invention spatial light modulator device in the binary mode 160 is a liquid crystal device. Such liquid crystal devices are of the same type used in pocket size television receivers. These liquid crystal devices are generally employed in a gray scale mode, however with the proper drive signals they can provide spatial light modulation in the binary mode by operation at the extremes of their gray scale range.

The output of the nonlinear joint transform image correlator of the present invention is provided using a second light source 150, which produces coherent light in the same manner as light source 110. This coherent light is employed to illuminate spatial light modulator device in the binary mode 160. Spatial light modulator device in the binary mode 160 is disposed at the object plane of a second Fourier transform lens system 170. A linear polarizer 165 is disposed between the spatial light modulator device in the binary mode 160 and Fourier transform lens system 170 to enhance the spatial light modulation contrast. The correlation output of the nonlinear joint transform image correlator is read at the Fourier plane 175 of second Fourier transform lens system 170. A second imaging device 180, similar to imaging device 135, may be disposed at this Fourier plane 175 to capture the correlation output.

The nonlinear joint transform image correlator of the present invention operates as follows. Let $r(x+x_0,y)$ be the reference image and let $s(x-x_0, y)$ be the input image for the coordinates (x,y). The light distribution at the Fourier plane of Fourier transform lens system 130 (that is, at the imaging device 135) is the interference of the Fourier transforms of the two images:

$$G(\alpha, \beta) = S\left(\frac{2\pi}{\lambda f}\alpha, \frac{2\pi}{\lambda f}\beta\right)\exp\left(-i\frac{2\pi}{\lambda f}x_0\alpha\right) +$$

$$R\left(\frac{2\pi}{\lambda f}\alpha, \frac{2\pi}{\lambda f}\beta\right)\exp\left(i\frac{2\pi}{\lambda f}x_0\alpha\right)$$

where $\alpha$ and $\beta$ are the spatial frequency coordinates, R(*) is the Fourier transform of the input image r(x,y), S(*) is the Fourier transform of the input image s(x,y), f is the focal length of Fourier transform lens system 130, and x is the wavelength of the light produced by light source 110. The Fourier transform intensity distribution at the imaging device 135 is given by:

$$|G(\alpha, \beta)|^2 =$$

$$\left|S\left(\frac{2\pi}{\lambda f}\alpha, \frac{2\pi}{\lambda f}\beta\right)\right|^2 + \left|R\left(\frac{2\pi}{\lambda f}\alpha, \frac{2\pi}{\lambda f}\beta\right)\right|^2 +$$

$$S\left(\frac{2\pi}{\lambda f}\alpha, \frac{2\pi}{\lambda f}\beta\right)R^*\left(\frac{2\pi}{\lambda f}\alpha,\right.$$

$$\left.\frac{2\pi}{\lambda f}\beta\right)\exp\left(-i\frac{2\pi}{\lambda f}2x_0\alpha\right) + S^*\left(\frac{2\pi}{\lambda f}\alpha,\right.$$

-continued $$\left.\frac{2\pi}{\lambda f}\beta\right)R\left(\frac{2\pi}{\lambda f}\alpha, \frac{2\pi}{\lambda f}\beta\right)\exp\left(i\frac{2\pi}{\lambda f}2x_0\alpha\right)$$

The correlation of the input images can be formed by taking the inverse Fourier transform of this interference intensity. The inverse Fourier transform of this interference intensity is produced in the preferred embodiment of the present invention using a spatial light modulation operating in a binary mode and a second coherent light source. The light of the second coherent light source is spatially modulated in accordance with this interference intensity distribution and supplied to a second Fourier transform lens system. The image resulting at the Fourier plane of this second Fourier transform lens system is the correlation output.

The present invention employs a thresholding network at the Fourier plane that binarizes the Fourier transform interference intensity. Thus a spatial light modulator operating in a binary mode can be used to read out the thresholded Fourier transform interference intensity in the inverse Fourier transform operation. In the prior art, gray scale spatial light modulation of the Fourier transform interference intensity was believed necessary to provide the correlation output. Thus it was not believed feasible to employ a spatial light modulator operating in a binary mode in such a system. In accordance with the present invention, however, the Fourier transform interference intensity is binarized and used to control a spatial light modulator operating in a binary mode. The Fourier transform interference intensity is binarized to:

$$H(\alpha, \beta) = \begin{cases} +1 & \text{if } |G(\alpha, \beta)|^2 > v \\ -1 & \text{otherwise} \end{cases}$$

where v is the threshold value.

Figure 3:
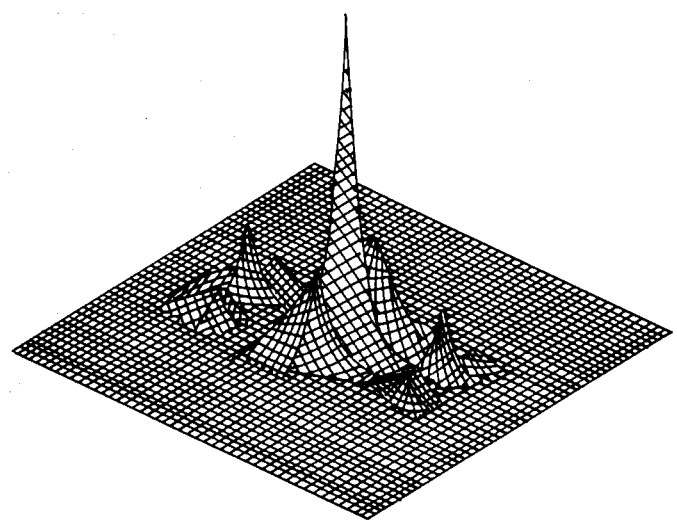
FIG. 3 illustrates the auto-correlation intensity obtained from images of the characters "F" in the case of the prior art.
Figure 4:
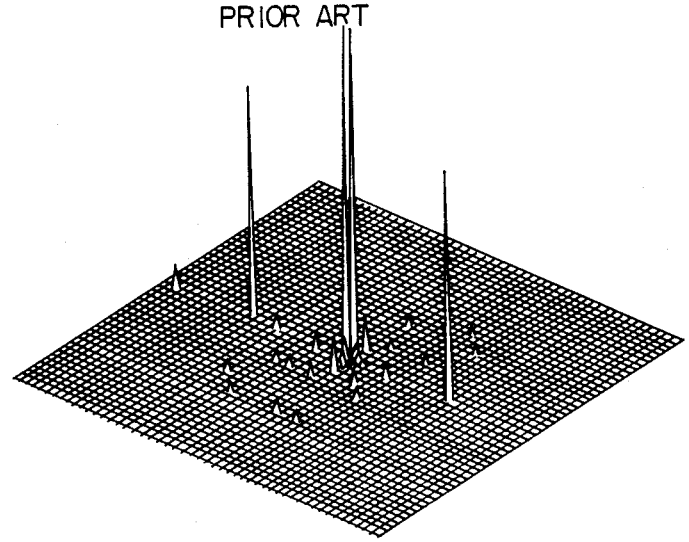
FIG. 4 illustrates the auto-correlation intensity obtained from images of the characters "F" in the case of the nonlinear joint transform image correlator of the present invention.
Figure 5:
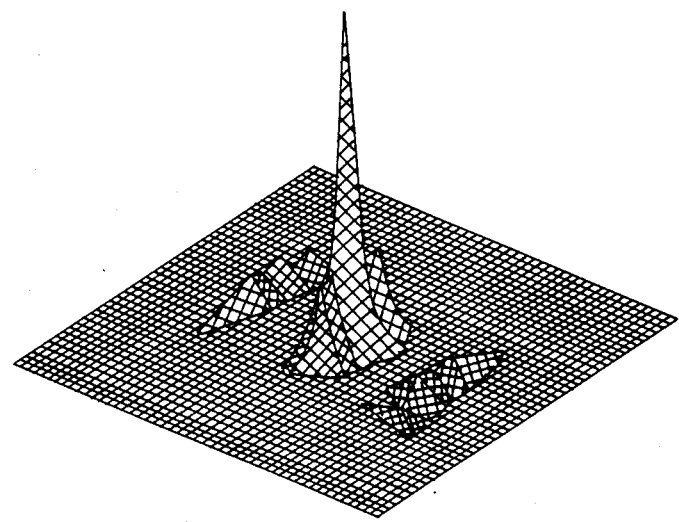
FIG. 5 illustrates the cross-correlation intensity obtained from images of the characters "F" and "L" in the case of the prior art.
Figure 6:
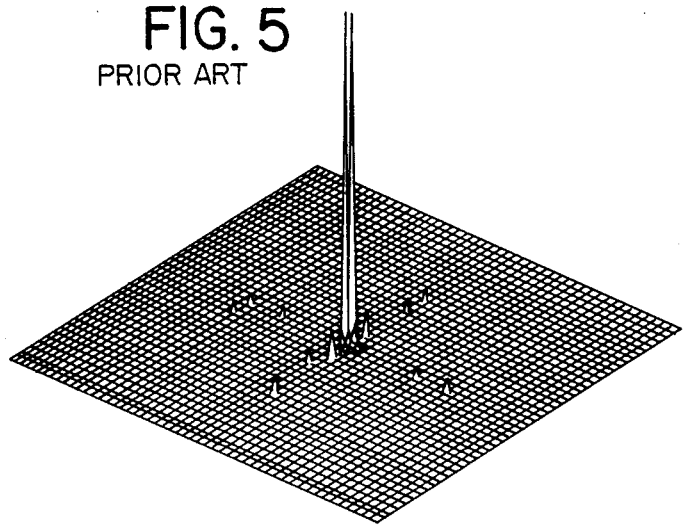
FIG. 6 illustrates the cross-correlation intensity obtained from images of the characters "F" and "L" in the case of the joint transform image correlator of the present invention.

FIGS. 3, 4, 5 and 6 illustrate a computer simulation of the nonlinear joint transform image correlator of the present invention. FIG. 3 illustrates the auto-correlation of the character "F" in accordance with the prior art. FIG. 4 illustrates a similar auto-correlation in accordance with the binarized joint Fourier transform of the present invention. FIG. 5 illustrates the cross-correlation of the characters "F" and "L" in accordance with the prior art. FIG. 6 illustrates the cross-correlation of the characters "F" and "L" in accordance with the binarized joint Fourier transform of the present invention as illustrated in FIG. 1.

FIGS. 3 and 4 illustrate a comparison of the auto-correlation for the prior art and the present invention, respectively. These figures have been scaled to show identical peak correlation. Note that the present invention yields lower auto-correlation sidelobes than the prior art.

Further advantages of the present invention over the prior art are shown in Table 1. Not evident from the scaled FIGS. 3 and 4 is the fact that the binarized joint Fourier transform correlator of the present invention provides increased intensity of the peak auto-correlation.

TABLE 1

| Correlator | Auto-correlation Comparison | | | |
|---|---|---|---|---|
| | $Ro^2$ | $Ro^2/SL^2$ | $DC/Ro^2$ | BW (x'-y') |
| Prior Art | 1.0 | 3.62 | 4.0 | (7-7) |
| Binarized | $1.51*10^5$ | 11.6 | 1.43 | (1-1) |

In Table 1, $Ro^2$ is the auto-correlation peak intensity, $SL^2$ is the largest sidelobe intensity, DC is the maximum intensity value for the zero order term in the correlation plane, and BW is the full correlation bandwidth determined in the x and y directions.

It can be seen from Table 1 that the thresholding of the Fourier transform interference intensity has improved the figures of merit for the auto-correlation case. The correlation peak intensity is considerably increased in the present invention. The ratio of the peak correlation intensity to the largest sidelobe intensity is increased from 3.62 to 11.6 in the present invention. The ratio of the the maximum zero order intensity to the peak interference intensity is decreased from 4 to 1.43 in the present invention. The x-y bandwidth of the auto-correlation function is likewise improved from a 7 by 7 pixel bandwidth in the prior art to a 1 by 1 pixel bandwidth in accordance with the present invention.

FIGS. 5 and 6 illustrate a computer simulation of the nonlinear joint transform image correlator of the present invention. FIG. 5 illustrates the cross-correlation between the characters "F" and "L" as illustrated in FIG. 1 in accordance with the prior art. FIG. 6 illustrates a similar cross-correlation in accordance with the binarized joint Fourier transform of the present invention. These figures have been scaled to show identical peak correlation.

Further advantages of the present invention over the prior art in the cross-correlation case are shown in Table 2. Not evident from the scaled FIGS. 5 and 6 is the fact that the binarized joint Fourier transform correlator of the present invention provides increased intensity of the peak cross-correlation.

TABLE 2

| Correlator | Cross-correlation Comparison | | |
|---|---|---|---|
| | $Rc^2$ | $Ro^2/Rc^2$ | $(1 - Rc^2/Ro^2)*100$ |
| Prior Art | 0.276 | 3.62 | 72.37 |
| Binarized | $7.88*10^3$ | 19.2 | 94.8 |

In Table 2, $Rc^2$ is the maximum intensity of the cross-correlation, $Ro^2/Rc^2$ is ratio of the maximum intensity of the auto-correlation ($Ro^2$) to the maximum intensity of the cross-correlation, and $(1-Rc^2/Ro^2)*100$ is the percentage difference between the peaks of the auto-correlation and the cross-correlation. It can be seen that each of these measures of correlation merit is improved in the present invention over the prior art.

Figure 7:
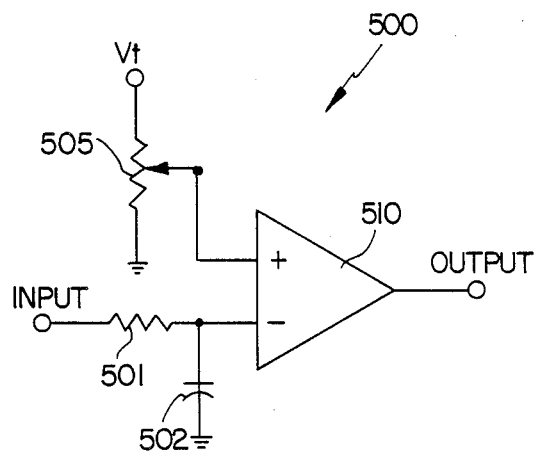
FIG. 7 illustrates an alternative embodiment of the thresholding network illustrated in FIG. 1.

FIG. 7 illustrates a alternative embodiment of the thresholding network 140 illustrated in FIG. 1. This thresholding network 500 includes a comparator 510. This comparator is preferably of the type designated LM106. The output from the imaging device 135 is applied to the inverting input through a time constant network consisting of resistor 501 and capacitor 502. This time constant network is optional and is employed to control the response time of the thresholding network 500. The voltage from a voltage divider potentiometer 505 is applied to the noninverting input of the comparator 510. The setting of the potentiometer determines the threshold of the thresholding network 500. This thresholding network 500 is very simple and easy to implement.

FIG. 8 illustrates an alternative embodiment of the present invention. Parts which correspond to parts previously illustrated in FIG. 1 have like reference numbers in FIG. 8. In this alternative embodiment an optically addressed spatial light modulator operating in the binary mode 190 is disposed at the Fourier plane of Fourier transform lens system 130. In conjunction with linear polarizer 195, optically addressed spatial light modulator operating in the binary mode 190 replaces the imaging device 135, the thresholding network 140, the computer interface 145 and the spatial light modulator operating in the binary mode 160 of FIG. 1. Optically addressed spatial light modulator operating in the binary mode 190 is a nonlinear optical material, such as an optical crystal, with a very high contrast. Light from Fourier transform lens system 130 forms the Fourier transform interference intensity at plane of optically addressed spatial light modulator operating in the binary mode 190. In accordance with this embodiment of the present invention, the thresholding operation takes place in optically addressed spatial light modulator operating in the binary mode 190. Light is passed or substantially blocked in accordance with the received light intensity due to the nonlinear, high contrast character of optically addressed spatial light modulator operating in the binary mode 190. The light emerging from optically addressed spatial light modulator operating in the binary mode 190 is the equivalent of the light emerging from spatial light modulator in the binary mode 160 illustrated in FIG. 1. This emergent light is then processed in the same manner as illustrated in FIG. 1 with the correlation results appearing at correlation plane 175.

A yet further embodiment of the present invention is illustrated in FIG. 9. In the embodiment illustrated the inverse Fourier transform of the Fourier transform interference intensity is formed via a computer. The output from thresholding network 140 is applied to an inverse Fourier transform circuit 210. This is a computer circuit constructed to produce the inverse Fourier transform of the thresholded Fourier transform interference intensity received from thresholding network 140. The output of inverse Fourier transform circuit 210 is supplied to display driver 220 and hence to visual display 225. This causes visual display 225 to display the computed correlation of the reference and input images.

In a further embodiment of the present invention, the thresholded light intensity values are selected from one of three ranges rather than from one of two ranges as previously described. Any of the previously illustrated structures could be employed with the addition of a three range thresholding means and driving the spatial light modulator at the Fourier plane in a trinary mode rather that in the previously described binary mode.

Multiple input objects and multiple reference objects can be processed simultaneously with this invention.

The spatial light modulators 120 and 125 can operate in the binary mode. In this case, the reference and input images are thresholded according to a predetermined threshold value.

I claim:

1. A nonlinear joint transform image correlator comprising:
   a joint image production means for producing a collimated joint image of a reference image and an input image;

a first Fourier transform lens device disposed to receive said collimated joint image at an object plane thereof and to produce the interference between the Fourier transforms of said reference image and said input image at a Fourier plane thereof;

an image detector means located at said Fourier plane of said first Fourier transform lens device, said image detector means including a plurality of detection cells disposed in a planar array at said Fourier plane, each of said detection cells generating an indication of the light intensity of said interference of said Fourier transforms of said reference image and said input image at said detection cell;

a threshold device connected to each detection cell of said image detector means for determining if the light intensity detected by each detection cell is greater than a threshold value, thereby generating a thresholded indication of the light intensity of said interference of said Fourier transforms of said reference image and said input image at said detection cell; and inverse Fourier transform means connected to said thresholding means for producing the inverse Fourier transform of said thresholded indication of the light intensity of said interference of said reference image and said input image, said inverse Fourier transform being the correlation between said reference image and said input image.

2. The nonlinear joint transform image correlator claimed in claim 1, wherein said joint image production means includes:

a reference image spatial light modulator having a plurality of light modulation cells disposed in a planar array within said object plane of said first Fourier transform lens device, said light modulation cells having transparency states corresponding to said reference image;

an input image spatial light modulator having a plurality of light modulation cells disposed in a planar array within said object plane of said first Fourier transform lens device adjacent to said planar array of said reference image spatial light modulator, said light modulation cells having transparency states corresponding to said input image; and an input source of collimated light disposed to illuminate said reference and image spatial light modulators, whereby said first Fourier transform lens device receives light from said image source as modified by said reference image spatial light modulator and said input image spatial light modulator.

3. The nonlinear joint transform image correlator claimed in claim 1, wherein said joint image production means includes:

an image spatial light modulator having a plurality of light modulation cells disposed in a planar array within said object plane of said first Fourier transform lens device, said image spatial light modulator including a reference image portion having light modulation cells having transparency states corresponding to said reference image and an input image portion adjacent to said reference image potion having light modulation cells having transparency states corresponding to said input image; and an input source of collimated light disposed to illuminate said reference and image spatial light modulators, whereby said first Fourier transform lens device receives light from said image source as modified by said image spatial light modulator.

4. The nonlinear joint transform image correlator claimed in claim 1, wherein said image detector means consists of a charge coupled device.

5. The nonlinear joint transform image correlator claimed in claim 1, wherein:

said threshold device further includes:

a threshold setting means for setting said threshold value based upon a statistical measure of the central tendency of the said indication of the light intensity at said detection cells.

6. The nonlinear joint transform image correlator claimed in claim 5, wherein:

said threshold setting means includes means for quantizing said indication of light intensity of said detection cells, means for forming a histogram of said quantized indications of light intensity and means for determining the median of said histogram, and means for setting said threshold value to said median.

7. The nonlinear joint transform image correlator claimed in claim 1, wherein:

said inverse Fourier transform means includes a Fourier plane spatial light modulator connected to said threshold device having a plurality of light modulation cells disposed in a planar array, each light modulation cell corresponding to a predetermined one of said detection cells, each light modulator cell operating in a binary mode having a first transparency state if the light intensity detected by said corresponding detection cell is greater than said threshold value and having a second transparency state if the light intensity detected by said corresponding detection cell is not greater than said threshold value, an output source of collimated light disposed to illuminate said Fourier plane spatial light modulator, and a second Fourier transform lens device disposed to receive said collimated light from said Fourier plane spatial light modulator at an object plane thereof, the correlation output of said nonlinear joint transform image correlator appearing at a Fourier plane thereof.

8. The nonlinear joint transform image correlator claimed in claim 7, wherein:

said Fourier plane spatial light modulator consists of a magneto-optic device.

9. The nonlinear joint transform image correlator claimed in claim 7, wherein:

said Fourier plane spatial light modulator consists of a gray scale liquid crystal device operated in saturation.

10. The nonlinear joint transform image correlator claimed in claim 7, further comprising:

a second image detector means located at said Fourier plane of said second Fourier transform lens device, said second image detector means including a plurality of detection cells disposed in a planar array at said Fourier plane, each of said detection cells generating an indication of the light intensity of the correlation signal a said detection cell.

11. The nonlinear joint transform image correlator claimed in claim 1, wherein:

said inverse Fourier transform means includes a computer circuit connected to said thresholding network for forming the inverse Fourier transform of said thresholded indication of the light intensity of said interference of said reference image and said output image.

12. The nonlinear joint transform image correlator claimed in claim 11, wherein:
said inverse Fourier transform means further includes a visual display device connected to said computer circuit for producing a visual display of said inverse Fourier transform of said thresholded indication of the light intensity of said interference of said reference image and said input image formed by said computer circuit.

13. A nonlinear joint transform image correlator comprising:
a joint image production means for producing a collimated joint image of a reference image and an input image;
a first Fourier transform lens device disposed to receive said collimated joint image at an object plane thereof and to produce the interference between the Fourier transforms of said reference image and said input image at a Fourier plane thereof;
an optically addressed spatial light modulator operating in the binary mode including a plurality of nonlinear light modulator cells of high contrast disposed at said Fourier plane of said first Fourier transform lens device, each light modulator cell having a first transparency state if the light intensity thereon is greater than a predetermined threshold value and having a second transparency state of the light intensity thereon is not greater than said predetermined threshold value, thereby transmitting light therethrough based upon the relation of the light intensity of said interference between the Fourier transforms of said reference image and said input image to said predetermined threshold value for each light modulator cell; an
a second Fourier transform lens device disposed to receive light transmitted from said optically addressed spatial light modulator at an object plane thereof, the correlation output of said nonlinear joint transform image correlator appearing at a Fourier plane thereof.

14. A nonlinear joint transform image correlator comprising:
a joint image production means for producing a collimated joint image of a reference image and an input image;
a first Fourier transform lens device disposed to receive said collimated joint image at an object plane thereof and to produce the interference between the Fourier transforms of said reference image and said input image at a Fourier plane thereof;
an image detector means located at said Fourier plane of said first Fourier transform lens device, said image detector means including a plurality of detection cells disposed in a planar array at said Fourier plane, each of said detection cells generating an indication of the light intensity of said interference of said Fourier transforms of said reference image and said input image at said detection cell;
a threshold device connected to each detection cell of said image detector means for determining if the light intensity detected by each detection cell is within one of three intensity ranges, thereby generating a thresholded indication of the light intensity of said interference of said Fourier transforms of said reference image and said input image at said detection cell; and
inverse Fourier transform means connected to said thresholding means for producing the inverse Fourier transform of said thresholded indication of the light intensity of said interference of said reference image and said input image, said inverse Fourier transform being the correlation between said reference image and said input image.

15. A method of forming a nonlinear joint transform image correlation, comprising the steps of:
producing a collimated joint image of a reference image and an input image;
forming the Fourier transform of said collimated joint image using a first Fourier transform lens device disposed to receive said collimated joint image at an object plane thereof and to produce the interference between the Fourier transforms of said reference image and said input image at a Fourier plane thereof;
detecting the Fourier transform interference intensity at said Fourier plane of said first Fourier transform lens device, including detection of the Fourier transform interference light intensity at a plurality of detection cells disposed in a planar array at said Fourier plane;
determining if the detected light intensity of each cell is greater than a threshold value, thereby generating a thresholded indication of the light intensity of said interference of said Fourier transforms of said reference image and said input image at said detection cell; and
forming the inverse Fourier transform of said thresholded indication of the light intensity of said interference of said reference image and said input image, said inverse Fourier transform being the correlation between said reference image and said input image.

16. The method of forming a nonlinear joint transform image correlation as claimed in claim 15, wherein:
said step of forming the inverse Fourier transform includes
producing a beam of collimated coherent light,
spatial light modulating said collimated coherent light via a plurality of light modulation cells, each light modulation cell operating in a binary mode having a first transparency state if the detected light intensity of a corresponding detection cell is greater than said threshold value and having a second transparency state if the detected light intensity of said corresponding detection cell is not greater than said threshold value,
forming the inverse Fourier transform of said spatial light modulated collimated coherent light using a second Fourier transform lens device disposed to receive said spatial light modulated collimated coherent light at an object plane thereof and to produce the correlation results at a Fourier plane thereof, and
reading the correlation output at said Fourier plane of said second Fourier transform lens system.

17. A method of forming a nonlinear joint transform image correlation, comprising the steps of:
producing a collimated joint image of a reference image and an input image;
forming the Fourier transform of said collimated joint image using a first Fourier transform lens device disposed to receive said collimated joint image at an object plane thereof and to produce the interference between the Fourier transforms of said reference image and said input image at a Fourier plane thereof;

detecting the Fourier transform interference intensity a said Fourier plane of said first Fourier transform lens device, including detection of the Fourier transform interference light intensity at a plurality of detection cells disposed in a planar array at said Fourier plane;

determining if the detected light intensity of each cell is within one of three intensity ranges, thereby generating a thresholded indication of the light intensity of said interference of said Fourier transforms of said reference image and said input image at said detection cell; and forming the inverse Fourier transform of said thresholded indication of the light intensity of said interference of said reference image and said input image, said inverse Fourier transform being the correlation between said reference image and said input image.

* * * * *